United States Patent
Xu et al.

(10) Patent No.: US 6,306,445 B1
(45) Date of Patent: Oct. 23, 2001

(54) METHODS FOR USING DEHYDROGENASES IN BAKING

(75) Inventors: Feng Xu, Woodland, CA (US); Peter Wagner, Copenhagen (DK)

(73) Assignees: Novozymes Biotech Inc., Davis, CA (US); Novozymes A/S, Bagsvaerd (DK)

( * ) Notice: Subject to any disclaimer, the term of this patent is extended or adjusted under 35 U.S.C. 154(b) by 0 days.

(21) Appl. No.: 09/311,687

(22) Filed: May 13, 1999

Related U.S. Application Data

(63) Continuation-in-part of application No. 09/078,183, filed on May 13, 1998, now abandoned.

(51) Int. Cl.$^7$ .................................................... A21D 2/00
(52) U.S. Cl. ................................ 426/20; 426/18; 426/19; 426/549
(58) Field of Search ................................. 426/20, 18, 19, 426/549

(56) References Cited

U.S. PATENT DOCUMENTS 4,683,198 * 7/1987 Ishikawa et al. ...................... 435/22

OTHER PUBLICATIONS

Kaid et al., 455939 Frosti, abstracting Cereal Chemistry, 1997, (Sep.–Oct.), 74 (5), 605–611.*

Walther et al. 88(02):M0020, abstracting Journal of Cereal Science, 1987, 5 (3) 299–305.*

Dong et al., 95(07):M0077 FSTA, abstracting Cereal Chemistry, 1995, 72(1), 58–64.*

* cited by examiner

*Primary Examiner*—Leslie Wong
(74) *Attorney, Agent, or Firm*—Robert L. Starnes

(57) ABSTRACT

The present invention relates to methods for preparing a dough, including incorporating into the dough a composition containing an effective amount of one or more dehydrogenases which improve one or more properties of the dough or a baked product obtained from the dough. The present invention also relates to methods for preparing a baked product. The present invention also relates to compositions containing an effective amount of one or more dehydrogenases for improving one or more properties of a dough and/or a baked product obtained from the dough. The present invention further relates to doughs or baked products and to pre-mixes for a dough.

24 Claims, No Drawings

METHODS FOR USING DEHYDROGENASES IN BAKING

CROSS-REFERENCE TO RELATED APPLICATION

This application is a continuation-in-part of pending U.S. application Ser. No. 09/078,183 filed on May 13, 1998, now abandoned, which application is fully incorporated herein by reference.

BACKGROUND OF THE INVENTION

1. Field of the Invention

The present invention relates to methods for preparing a dough and/or baked product with a dehydrogenase.

2. Description of the Related Art

The strength of a dough is an important aspect of baking for both small-scale and large-scale applications. A strong dough has a greater tolerance of mixing time, proofing time, and mechanical vibrations during dough transport, whereas a weak dough is less tolerant to these treatments. A strong dough with superior rheological and handling properties results from flour containing a strong gluten network. Flour with a low protein content or a poor gluten quality results in a weak dough.

Dough "conditioners" are well known in the baking industry. The addition of conditioners to bread dough has resulted in improved machinability of the dough and improved texture, volume, flavor, and freshness (anti-staling) of the bread. Nonspecific oxidants, such as iodates, peroxides, ascorbic acid, potassium bromate and azodicarbonamide have a gluten strengthening effect. It has been suggested that these conditioners induce the formation of interprotein bonds which strengthen the gluten, and thereby the dough. However, the use of several of the currently available chemical oxidizing agents has been met with consumer resistance or is not permitted by regulatory agencies.

The use of enzymes as dough conditioners has been considered as an alternative to chemical conditioners. A number of enzymes have been used recently as dough and/or bread improving agents, in particular, enzymes that act on components present in large amounts in the dough. Examples of such enzymes are amylases, proteases, glucose oxidases, and (hemi)cellulases, including pentosanases.

The class of enzymes known as "oxidoreductases" (Class 1) is defined by the Nomenclature Committee of the International Union of Biochemistry on the Nomenclature and Classification of Enzymes (Enzyme Nomenclature, Academic Press, New York, 1992) as all enzymes which catalyze oxido-reductions. The substrate oxidized is regarded as a hydrogen or electron donor. The classification is based on 'donor:acceptor oxidoreductase'. The recommended name is 'dehydrogenase'. However, 'oxidase' (EC 1.X.3.1) is used only for cases where $O_2$ is acceptor, and 'oxygenase' only for cases where the molecule $O_2$ is directly incorporated into the substrate. 'Peroxidase' is used specifically for enzymes using $H_2O_2$ as acceptor (EC 1.11.X.Y).

Dehydrogenases typically catalyze the oxidation of a CH—OH, aldehyde, oxo, CH—$NH_2$, CH—NH, CH—CH, sulphur, or heme (haem) group. Depending on the nature of the electron acceptor, this enzyme family can be divided into the following two sub-families: (1) NAD(P)$^+$-dependent and (2) NAD(P)$^+$-independent. The first group includes aliphatic/aromatic/carbohydrate alcohol:NAD(P)$^+$ dehydrogenases (such as xylose-1-dehydrogenase); and the second group includes donor:quinone dehydrogenases (such as cellobiose dehydrogenase), donor:cytochrome dehydrogenases (such as L-lactic dehydrogenase), and other dehydrogenases which use a disulphide compound or an iron-sulphur protein as an acceptor. Most NAD(P)-independent dehydrogenases (such as fructose dehydrogenase) use flavin compounds as their prosthetic groups, alone or in combination with a heme, although some dehydrogenases (such as glucose dehydrogenase EC 1.1.99.17) apparently do not employ flavin in their catalyses.

It is the object of the present invention to improve the properties of dough and/or baked products by the use of a dehydrogenase.

SUMMARY OF THE INVENTION

The present invention relates to methods for preparing a dough, comprising incorporating into the dough an effective amount of one or more dehydrogenases, wherein each dehydrogenase is independently:

(a) a NAD(P)-independent dehydrogenase selected from the group consisting of a donor:quinone dehydrogenase (E.C. 1.1.5 and 1.1.99), donor:cytochrome dehydrogenase (E.C. 1.1.2), aldehyde:pyrroloquinoline-quinone (E.C. 1.2.99.3); succinate:ubiquinone dehydrogenase (E.C. 1.3.5.1); succinate dehydrogenase (E.C. 1.3.99.1); primary amine dehydrogenase (E.C. 1.4.99.3); sarcosine dehydrogenase (1.5.99.1); dimethylglycine dehydrogenase (E.C. 1.5.99.2); nicotine dehydrogenase (E.C. 1.5.99.4); spermidine dehydrogenase (E.C. 1.5.99.6); proline dehydrogenase (E.C. 1.5.99.8); monodehydroascorbate reductase (E.C. 1.6.5.4); NAD(P)H:quinone dehydrogenase (E.C. 1.6.99.2); and ubiquinol:ferricytochrome-c dehydrogenase (E.C. 1.10.2.2); and (b) a NAD(P)-dependent dehydrogenase.

The present invention also relates to methods for preparing a baked product.

The present invention also relates to compositions comprising an effective amount of one or more dehydrogenases, for improving one or more properties of a dough and/or a baked product obtained from the dough, and a carrier and/or a baking ingredient.

The present invention also relates to doughs or baked products.

The present invention further relates to pre-mixes for a dough comprising an effective amount of one or more dehydrogenases, for improving one or more properties of a dough and/or a baked product obtained from the dough, and a carrier and/or a baking ingredient.

DETAILED DESCRIPTION OF THE INVENTION

The present invention relates to methods for preparing a dough and/or a baked product comprising incorporating into the dough an effective amount of one or more dehydrogenases which improve one or more properties of the dough and/or the baked product obtained from the dough relative to a dough or a baked product in which a dehydrogenase is not incorporated.

The phrase "incorporating into the dough" is defined herein as adding the dehydrogenase(s) to the dough, any ingredient from which the dough is to be made, and/or any mixture of dough ingredients from which the dough is to be made. In other words, the dehydrogenase(s) may be added in any step of the dough preparation and may be added in one, two, or more steps.

The term "effective amount" is defined herein as an amount of dehydrogenase(s) that is sufficient for providing a measurable effect on at least one property of interest of the dough and/or baked product.

The term "improved property" is defined herein as any property of a dough and/or a product obtained from the dough, particularly a baked product, which is improved by the action of a dehydrogenase relative to a dough or product in which a dehydrogenase is not incorporated. The improved property may include, but is not limited to, increased strength of the dough, increased elasticity of the dough, increased stability of the dough, reduced stickiness of the dough, improved extensibility of the dough, improved machinability of the dough, increased volume of the baked product, improved crumb structure of the baked product, improved softness of the baked product, improved flavor of the baked product, and/or improved antistaling of the baked product.

The use of a dehydrogenase(s) may result in an increased strength, stability, and/or reduced stickiness of the dough, resulting in improved machinability, as well as in an increased volume, improved crumb structure, and/or softness of the baked product. The effect on the dough may be particularly advantageous when a poor quality flour is used.

Improved machinability is of particular importance in connection with dough that is to be processed industrially.

The improved property may be determined by comparison of a dough and/or a baked product prepared with and without addition of one or more dehydrogenases in accordance with the methods of the present invention. Techniques which can be used to determine improvements achieved by use of the methods of present invention are described below in the Examples. Organoleptic qualities may be evaluated using procedures well established in the baking industry, and may include, for example, the use of a panel of trained taste-testers.

The term "increased strength of the dough" is defined herein as the property of a dough that has generally more elastic properties and/or requires more work input to mould and shape the dough.

The term "increased elasticity of the dough" is defined herein as the property of a dough which has a higher tendency to regain its original shape after being subjected to a certain physical strain.

The term "increased stability of the dough" is defined herein as the property of a dough that is less susceptible to mechanical abuse thus better maintaining its shape and volume.

The term "reduced stickiness of the dough" is defined herein as the property of a dough that has less tendency to adhere to surfaces, e.g., in the dough production machinery, and is either evaluated empirically by the skilled test baker or measured by the use of a texture analyzer (e.g., TAXT2) known in the art.

The term "improved extensibility of the dough" is defined herein as the property of a dough that can be subjected to increased strain or stretching without rupture.

The term "improved machinability of the dough" is defined herein as the property of a dough that is generally less sticky and/or more firm and/or more elastic.

The term "increased volume of the baked product" is measured as the specific volume of a given loaf of bread (volume/weight) determined typically by the traditional rape seed displacement method.

The term "improved crumb structure of the baked product" is defined herein as the property of a baked product with finer and/or thinner cell walls in the crumb and/or more uniform/homogenous distribution of cells in the crumb and is usually evaluated empirically by the skilled test baker.

The term "improved softness of the baked product" is the opposite of "firmness" and is defined herein as the property of a baked product that is more easily compressed and is evaluated either empirically by the skilled test baker or measured by the use of a texture analyzer (e.g., TAXT2) known in the art.

The term "improved flavor of the baked product" is evaluated by a trained test panel.

The term "improved antistaling of the baked product" is defined herein as the properties of a baked product that have a reduced rate of deterioration of quality parameters, e.g., softness and/or elasticity, during storage.

In a preferred embodiment, the one or more dehydrogenases improve one or more properties of the dough or the baked product obtained from the dough. In another preferred embodiment, the one or more dehydrogenases improve one or more properties of the dough and the baked product obtained from the dough.

In a preferred embodiment, the improved property is increased strength of the dough. In another preferred embodiment, the improved property is increased elasticity of the dough. In another preferred embodiment, the improved property is increased stability of the dough. In another preferred embodiment, the improved property is reduced stickiness of the dough. In another preferred embodiment, the improved property is improved extensibility of the dough. In another preferred embodiment, the improved property is improved machinability of the dough. In another preferred embodiment, the improved property is increased volume of the baked product. In another preferred embodiment, the improved property is improved crumb structure of the baked product. In another preferred embodiment, the improved property is improved softness of the baked product. In another preferred embodiment, the improved property is improved flavor of the baked product. In another preferred embodiment, the improved property is improved antistaling of the baked product.

The term "dough" is defined herein as a mixture of flour and other ingredients firm enough to knead or roll. The dough may be fresh, frozen, pre-bared, or pre-baked. The preparation of frozen dough is described by Kulp and Lorenz in *Frozen and Refrigerated Doughs and Batters*.

The term "baked product" is defined herein as any product prepared from a dough, either of a soft or a crisp character. Examples of baked products, whether of a white, light or dark type, which may be advantageously produced by the present invention are bread (in particular white, whole-meal or rye bread), typically in the form of loaves or rolls, French baguette-type bread, pasta, pita bread, tortillas, tacos, cakes, pancakes, biscuits, cookies, pie crusts, steamed bread, and crisp bread, and the like.

The term "dehydrogenase" as used in the present invention is defined herein as a dehydrogenase which (1) transfers two electrons as two hydrogen atoms from a donor to an acceptor; (2) does not utilize $O_2$ as an acceptor or does not utilize $O_2$ or peroxide as its primary acceptor; and (3) may utilize a cytochrome, quinone, disulphide compound, iron-sulphur protein, or inorganic/organic biological redox active compound as its primary acceptor.

Examples of dehydrogenases useful in the methods of the present invention are defined by the Nomenclature Committee of the International Union of Biochemistry on the Nomenclature and Classification of Enzymes and listed as enzyme subclasses E.C. 1.1.1, 1.1.2, 1.14, 1.1.5, 1.1.99, 1.2.1, 1.2.2, 1.2.4, 1.2.7, 1.2.99, 1.3.1, 1.3.2, 1.3.5, 1.3.7, 1.3.99, 1.4.1, 1.4.2, 1.4.4, 1.4.7, 1.4.99, 1.5.1, 1.5.99, 1.6.1, 1.6.2, 1.6.4, 1.6.5, 1.6.6, 1.6.7, 1.6.8, 1.6.99, 1.7.2, 1.7.7, 1.7.99, 1.8.1, 1.8.2, 1.8.4, 1.8.5, 1.8.7, 1.8.99, 1.9.3, 1.9.6, 1.9.99, 1.10.1, 1.10.2, 1.10.99, 1.12.1, 1.12.2, 1.12.7, 1.12.99, 1.17.1, 1.17.4, and 1.17.99.

In the methods of the present invention, any NAD(P)$^+$-independent or NAD(P)$^+$-dependent dehydrogenase described below may be used which possesses suitable enzyme activity in a pH and temperature range appropriate for making a dough and/or a baked product. It is preferable that the dehydrogenase(s) is active over broad pH and temperature ranges.

In a preferred embodiment, the dehydrogenase(s) has a pH optimum in the range of about 3 to about 10. In a more preferred embodiment, the dehydrogenase(s) has a pH optimum in the range of about 4.5 to about 8.5.

In a preferred embodiment, the dehydrogenase(s) has a temperature optimum in the range of about 5° C. to about 100° C. In a more preferred embodiment, the dehydrogenase (s) has a temperature optimum in the range of about 25° C. to about 75° C.

In a preferred embodiment, the dehydrogenase(s) is a NAD(P)$^+$-independent dehydrogenase. The NAD(P)$^+$-independent dehydrogenase may act on a CH—OH, aldehyde, CH—NH$_2$, CH=NH, CH—CH, or sulphur-iron as a donor. The acceptor may be a cytochrome, a quinone, a disulphide compound, an iron-sulphur protein, or an organic or an inorganic biological redox active compound. In a preferred embodiment, the acceptor is a quinone. The NAD(P)$^+$-independent dehydrogenases generally are flavin-, metal-, heme- (haem-), or pterin-containing enzymes.

In a more preferred embodiment, the NAD(P)$^+$-independent dehydrogenase is a donor:quinone dehydrogenase. In a most preferred embodiment, the donor:quinone dehydrogenase is a cellobiose dehydrogenase (E.C. 1.1.5.1). In another most preferred embodiment, the donor:quinone dehydrogenase is a choline dehydrogenase (E.C. 1.1.99.1). In another most preferred embodiment, the donor:quinone dehydrogenase is a D-gluconate dehydrogenase (E.C. 1.1.99.3). In another most preferred embodiment, the donor:quinone dehydrogenase is a 2-dehydro-D-gluconate dehydrogenase (E.C. 1.1.99.4). In another most preferred embodiment, the donor:quinone dehydrogenase is a glycerol-3-phosphate dehydrogenase (E.C. 1.1.99.5). In another most preferred embodiment, the donor:quinone dehydrogenase is a D-2-hydroxy acid dehydrogenase (E.C. 1.1.99.6). In another most preferred embodiment, the donor:quinone dehydrogenase is an alcohol dehydrogenase (E.C. 1.1.99.8). In another most preferred embodiment, the donor:quinone dehydrogenase is a pyrodoxine dehydrogenase (E.C. 1.1.99.9). In another most preferred embodiment, the donor:quinone dehydrogenase is a glucose dehydrogenase (E.C. 1.1.99.10). In another most preferred embodiment, the donor:quinone dehydrogenase is a fructose 5-dehydrogenase (E.C. 1.1.99.11). In another most preferred embodiment, the donor:quinone dehydrogenase is a sorbose dehydrogenase (E.C. 1.1.99.12). In another most preferred embodiment, the donor:quinone dehydrogenase is a glucoside-3 dehydrogenase (E.C. 1.1.9.13). In another most preferred embodiment, the donor:quinone dehydrogenase is a glycolate dehydrogenase (E.C. 1.1.99.14). In another most preferred embodiment, the donor:quinone dehydrogenase is a malate dehydrogenase (E.C. 1.1.99.16). In another most preferred embodiment, the donor:quinone dehydrogenase is a glucose:(pyrroloquinoline-quinone) dehydrogenase (E.C. 1.1.99.17). In another most preferred embodiment, the donor:quinone dehydrogenase is cellobiose dehydrogenase (E.C. 1.1.99.18). In another most preferred embodiment, the donor:quinone dehydrogenase is an alkan-1-ol dehydrogenase (E.C. 1.1.99.20). In another most preferred embodiment, the donor:quinone dehydrogenase is a D-sorbitol dehydrogenase (E.C. 1.1.99.21). In another most preferred embodiment, the donor:quinone dehydrogenase is a glycerol dehydrogenase (E.C. 1.1.99.22). In another most preferred embodiment, the donor:quinone dehydrogenase is a maltose dehydrogenase (U.S. Pat. No. 4,683,198). In another most preferred embodiment, the donor:quinone dehydrogenase is a cellobiose dehydrogenase (Schou et al., 1998, *Biochemical Journal* 3330: 565–571). In another most preferred embodiment, the donor:quinone dehydrogenase is a pyranose 2-dehydrogenase (Volc et al., 1977, *Archives of Microbiology* 167: 119–125). In another most preferred embodiment, the donor:quinone dehydrogenase is a glucose 3-dehydrogenase (Morrison et al., 1999, *Applied Microbiology and Biotechnology* 51: 58–64).

In another more preferred embodiment, the NAD(P)$^+$-independent dehydrogenase is a donor:cytochrome dehydrogenase. In a most preferred embodiment, the donor:cytochrome dehydrogenase is a lactate dehydrogenase (cytochrome) (E.C. 1.1.2.3). In another most preferred embodiment, the donor:cytochrome dehydrogenase is a mannitol dehydrogenase (E.C. 1.1.2.2).

In another more preferred embodiment, the NAD(P)$^+$-independent dehydrogenase is an aldehyde:pyrroloquinoline-quinone (E.C. 1.2.99.3); succinate:ubiquinone dehydrogenase (E.C. 1.3.5.1); succinate dehydrogenase (E.C. 1.3.99.1); primary amine dehydrogenase (E.C. 1.4.99.3); sarcosine dehydrogenase (1.5.99.1); dimethylglycine dehydrogenase (E.C. 1.5.99.2); nicotine dehydrogenase (E.C. 1.5.99.4); spermidine dehydrogenase (E.C. 1.5.99.6); proline dehydrogenase (E.C. 1.5.99.8); monodehydroascorbate reductase (E.C. 1.6.5.4); NAD(P) H:quinone dehydrogenase (E.C. 1.6.99.2); or ubiquinol:ferricytochrome-c dehydrogenase (E.C. 1.10.2.2).

The NAD(P)$^+$-independent dehydrogenases exert their effect on the dough and/or baked product obtained from the dough by enzyme-catalyzed oxidation of a reducing substrate such as a carbohydrate and the concomitant reduction of a suitable oxidizing substrate. In general, the reducing substrate transfers one or more electrons (or equivalent such as H or H$^-$) to, for example, the flavin or flavin/heme center of the dehydrogenase, which then transfers the electrons to the oxidizing substrate. The immediate products from the catalysis can initiate secondary reactions to affect properties of the dough and/or baked product. For example, the reduction of a quinone by the dehydrogenase to generate a semiquinone (or phenoxy radical) can then initiate a radical chain reaction among the gluten and/or lipid components of dough. Another example involves the oxidation of a saccharide to the corresponding lactone or carboxylic acid, which then can alter the starch:gluten:lipid:pentosan interactions in the dough as a result of the change in charge and/or hydrophobicity caused by the oxidation.

The reducing substrates preferably include mono-and oligo-saccharides (such as glucose, maltose, and maltotriose) and their derivatives (such as gluconolactone and methylglucopyranoside) as well as other alpha-hydroxy carboxylic acids (such as lactic acid). The oxidizing substrates may include redox-active organic compounds (such as benzoquinone, dichlorophenol-indophenol, other quinones, and nitroblue tetrazolium), inorganic compounds (such as potassium ferricyanide), and biological molecules (such as cytochrome c).

In another preferred embodiment, the dehydrogenase(s) is a NAD(P)$^+$-dependent dehydrogenase. The NAD(P)$^+$-dependent dehydrogenase may act on a CH—OH, aldehyde, CH—NH$_2$, CH=NH, CH—CH, sulphur, or haem (heme) group as a donor. The acceptor molecule is NAD and/or NADP$^+$.

In a more preferred embodiment, the NAD(P)$^+$-dependent dehydrogenase is an alcohol dehydrogenase (E.C. 1.1.1.1; E.C. 1.1.1.2). In another more preferred embodiment, the NAD(P)$^+$-dependent dehydrogenase is a lactate dehydrogenase (E.C. 1.1.1.27; E.C. 1.1.1.28). In another more preferred embodiment, the NAD(P)$^+$-dependent dehydrogenase is a glucose dehydrogenase (E.C. 1.1.1.47; E.C. 1.1.1.118; E.C. 1.1.1.119).

The NAD(P)$^+$-dependent dehydrogenases exert their effect on the dough and/or baked product obtained from the dough by enzyme-catalyzed oxidation of a reducing substrate contained in the dough or added to the dough. In general, the reducing substrate transfers one or more electrons (or equivalent such as H or H$^-$) to, for example, the flavin or flavin/heme center of the dehydrogenase, which then transfers the electrons to the oxidizing substrate. The immediate products from the catalysis can initiate secondary reactions to affect properties of the dough and/or baked product. For example, the reduction of NAD$^+$ or NADP$^+$ to NADH or NADPH, respectively, by a dehydrogenase may than result in the reaction of the NADH or NADPH with O$_2$ to generate a superoxide radical and initiate a radical chain reaction among the gluten and/or lipid components in the dough. Another example involves the oxidation of a saccharide to the corresponding lactone or carboxylic acid, which then can alter the starch:gluten:lipid:pentosan interactions in the dough as a result of the change in charge and/or hydrophobicity caused by the oxidation.

In the methods of the present invention, combinations of dehydrogenases may be used to improve one or more properties of the dough and/or baked product obtained from the dough. In a preferred embodiment, the combination comprises one or more NAD(P)$^+$-dependent dehydrogenases, one or more NAD(P)$^+$-independent dehydrogenases, or combinations of one or more NAD(P)$^+$-dependent dehydrogenases and one or more NAD(P)$^+$-independent dehydrogenases.

The source of a dehydrogenase is not critical for improving one or more properties of a dough and/or a baked product. Accordingly, the dehydrogenase(s) may be obtained from any source such as a plant, microorganism, or animal. The dehydrogenase(s) is preferably obtained, e.g., from a microbial source, such as a bacterium or a fungus, e.g., a filamentous fungus or a yeast.

In a preferred embodiment, the dehydrogenase(s) is obtained from a bacterial source. For example, the dehydrogenase(s) may be obtained from an Acetobacter, Acinetobacter, Agrobacterium, Alcaligenes, Arthrobacter, Azotobacter, Bacillus, Comamonas, Clostridium, Gluconobacter, Halobacterium, Mycobacterium, Rhizobium, Salmonella, Serratia, Streptomyces, E. coli, Pseudomonas, Wolinella, or methylotrophic bacterium strain.

In a more preferred embodiment, the dehydrogenase(s) is obtained from an *Acetobacter aceti, Alcaligenes faecalis, Arthrobacter oxidans, Azotobacter vinelandii, Bacillus alkalophilus, Bacillus amyloliquefaciens, Bacillus anitratum, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis, Bacillus thuringiensis, Comamonas testosteroni, Clostridum tyrobutyricum, Gluconobacter dioxyaceticus, Gluconobacter liquefaciens, Gluconobacter suboxydans, Halobacterium cutirubrum, Mycobacterium convolutum, Rhizobium melioti, Salmonella typhimurium, Serratia marcescens, Streptomyces lividans, Streptomyces murinus, Pseudomonas aeruginosa, Pseudomonas fluorescens, Pseudomonas putida*, or *Wolinella succinogens* strain.

In another preferred embodiment, the dehydrogenase(s) is obtained from a fungal source. For example, the dehydrogenase(s) may be obtained from a yeast strain such as a Candida, Kluyveromyces, Pichia, Saccharomyces, Schizosaccharomyces, or Yarrowia strain; or from a filamentous fungal strain such as an Acremonium, Aspergillus, Aureobasidium, Chrysosporium, Cryptococcus, Filibasidium, Fusarium, Humicola, Magnaporthe, Monilia, Mucor, Myceliophthora, Neocallimastix, Neurospora, Paecilomyces, Penicillium, Phanerochaete, Piromyces, Schizophyllum, Sclerotium, Sporotrichum, Talaromyces, Thermoascus, Thielavia, Tolypocladium, or Trichoderma strain.

In another more preferred embodiment, the dehydrogenase(s) is obtained from a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* strain.

In another more preferred embodiment, the dehydrogenase(s) is obtained from an *Aspergillus aculeatus, Aspergillus awamori, Aspergillus foetidus, Aspergillus japonicus, Aspergillus nidulans, Aspergillus niger, Aspergillus oryzae, Chrysosporium lignorum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sulphureum, Fusarium toruloseum, Fusarium trichothecioides, Fusarium venenatum, Humicola insolens, Humicola lanuginosa, Monilia sitophila, Mucor miehei, Myceliophthora thermophila, Neurospora crassa, Penicillium purpurogenum, Phanerochaete chrysporum, Polyporus pinsitus, Polyporus versicolor, Sclerotium rolsfii, Sporotrichum thermophile, Trichoderma citrinoviride, Trichoderma hamatum, Trichoderma harzianum, Trichoderma koningii, Trichoderma longibrachiatum, Trichoderma polysporum, Trichoderma reesei, Trichoderma saturnisporum*, or *Trichoderma viride* strain.

In a more preferred embodiment, the cellobiose dehydrogenase is obtained from *Humicola insolens*. In another more preferred embodiment, the fructose dehydrogenase is obtained from Gluconobacter sp. In another more preferred embodiment, the lactate dehydrogenase is obtained from *Saccharomyces cerevisiae*.

The dehydrogenase(s) may be obtained from the organism in question by any suitable technique, and in particular by use of recombinant DNA techniques known in the art (c.f. Sambrook, J. et aL, 1989, *Molecular Cloning, A Laboratory Manual*, Cold Spring Harbor Press, Cold Spring Harbor, N.Y., USA). The use of recombinant DNA techniques generally comprises cultivation of a host cell transformed with a recombinant DNA vector, consisting of the product gene of interest inserted between an appropriate promoter and terminator, in a culture medium under conditions permitting the expression of the enzyme and recovering the enzyme from the culture. The DNA sequence may be of genomic, cDNA, or synthetic origin, or any mixture of these, and may be isolated or synthesized in accordance with methods known in the art. The enzyme may also be obtained from its naturally occurring source, such as a plant or organism, or relevant part thereof. Furthermore, the dehydrogenase(s) may be obtained from commercial suppliers.

When a dehydrogenase is added to dough intended for use in the preparation of baked products, it may exert an oxidizing effect on dough constituents. The dehydrogenase(s) is used in an amount sufficient to provide the desired effect, i.e., the improved properties in question. Thus, the dosage of the dehydrogenase(s) to be used in the methods of the present invention should be adapted to the nature and composition of the dough in question as well as to the nature of the dehydrogenase(s) to be used.

The term "composition" is defined herein as a dough-improving and/or baked product-improving composition which, in addition to one or more dehydrogenases, comprise one or more additional substances conventionally used in baking. The additional substance(s) may be other enzymes or chemical additives known in the art to be useful in dough preparation and/or baking.

The bread-improving and/or dough improving composition of the invention is generally included in the dough in an amount corresponding to 0.01–5%, in particular 0.1–3%. The dehydrogenase(s) is typically added in an amount corresponding to 0.01–100 mg enzyme protein per kg of flour, preferably 0.1–25 mg enzyme protein per kg of flour, more preferably 0.1–10 mg enzyme protein per kg of flour, and most preferably 0.5–5 mg enzyme protein per kg of flour.

In terms of enzyme activity, the appropriate dosage of a given dehydrogenase for exerting a desirable improvement of dough and/or baked products will depend on the enzyme and the enzyme substrate in question. The skilled person may determine a suitable enzyme unit dosage on the basis of methods known in the art.

The dehydrogenase(s) and/or additional enzymes to be used in the methods of the present invention may be in any form suitable for the use in question, e.g., in the form of a dry powder, agglomerated powder, or granulate, in particular a non-dusting granulate, liquid, in particular a stabilized liquid, or protected enzyme. Granulates and agglomerated powders may be prepared by conventional methods, e.g., by spraying the dehydrogenase(s) onto a carrier in a fluid-bed granulator. The carrier may consist of particulate cores having a suitable particle size. The carrier may be soluble or insoluble, e.g., a salt (such as NaCl or sodium sulfate), sugar (such as sucrose or lactose), sugar alcohol (such as sorbitol), starch, rice, corn grits, or soy. The dehydrogenase(s) and/or additional enzymes may be contained in slow-release formulations. Methods for preparing slow-release formulations are well known in the art. Liquid enzyme preparations may, for instance, be stabilized by adding nutritionally acceptable stabilizers such as a sugar, sugar alcohol, or another polyol, and/or lactic acid or another organic acid according to established methods.

For inclusion in pre-mixes or flour it is advantageous that the dehydrogenase(s) is in the form of a dry product, e.g., a non-dusting granulate, whereas for inclusion together with a liquid it is advantageously in a liquid form.

A substrate of the dehydrogenase in question may also be incorporated into the dough. The substrate may be incorporated into dough separately or together with the dehydrogenase of interest, optionally as constituent(s) of the bread-improving and/or dough-improving composition.

Preferred substrates for a cellobiose dehydrogenase are cellobiose and lactose. A preferred substrate for a lactate dehydrogenase is lactate. A preferred substrate for a fructose dehydrogenase is fructose.

Alternatively, an enzyme which acts on a substance endogenous to the flour to produce a substrate for the dehydrogenase of interest may also be incorporated in the dough. Furthermore, the substance and the enzyme which acts on the substance to produce a substrate for the dehydrogenase of interest may also be incorporated in the dough. For example, glucose isomerase may be used to convert glucose to fructose, which then may serve as a substrate for fructose dehydrogenase.

The specific amount of the substrate available for the dehydrogenase of interest will depend on a number of factors, such as the baking process used, the length of time for mixing, fermentation, proofing and/or baking, the quality of the yeast and/or flour used, and the activity of any endogenous and exogenous enzymes present.

One or more additional enzymes may also be incorporated into the dough. The additional enzyme may be of any origin, including mammalian and plant, and preferably of microbial (bacterial, yeast or fungal) origin and may be obtained by techniques conventionally used in the art.

In a preferred embodiment, the additional enzyme may be an amylase, such as an alpha-amylase (useful for providing sugars fermentable by yeast and retarding staling) or beta-amylase, cyclodextrin glucanotransferase, peptidase, in particular, an exopeptidase (useful in flavour enhancement), transglutaminase, lipase (useful for the modification of lipids present in the dough or dough constituents so as to soften the dough), phospholipase (useful for the modification of lipids present in the dough or dough constituents so as to soften the dough and improve gas retention in the dough), cellulase, hemicellulase, in particular a pentosanase such as xylanase (useful for the partial hydrolysis of pentosans which increases the extensibility of the dough), protease (useful for gluten weakening in particular when using hard wheat flour), protein disulfide isomerase, e.g., a protein disulfide isomerase as disclosed in WO 95/00636, glycosyltransferase, peroxidase (useful for improving the dough consistency), laccase, or oxidase, e.g., an aldose oxidase, glucose oxidase, pyranose oxidase, lipoxygenase, or L-amino acid oxidase (useful in improving dough consistency).

The xylanase is preferably of microbial origin, e.g., derived from a bacterium or fungus, such as a strain of Aspergillus, in particular of *Aspergillus aculeatus*, *Aspergillus niger* (cf. WO 91/19782), *Aspergillus awamori* (WO 91/18977), or *Aspergillus tubigensis* (WO 92/01793), from a strain of Trichoderma, e.g., *Trichoderma reesei*, or from a strain of Humicola, e.g., *Humicola insolens* (WO 92/17573, the content of which is hereby incorporated by reference).

Commercially available amylases useful in the present invention are NOVAMYL™ (a *Bacillus stearothermophilus* maltogenic amylase, available from Novo Nordisk A/S, Denmark), FUNGAMYL® (an *Aspergillus oryzae* alpha-amylase, available from Novo Nordisk A/S, Denmark), and BAN™ (a *Bacillus licheniformis* alpha-amylase, available from Novo Nordisk A/S, Denmark). A commercially available amyloglucosidase useful in the present invention is AMG™ (an *Aspergillus niger* amyloglucosidase, available from Novo Nordisk A/S, Denmark). Other useful commercially available amylase products include GRINDAMYL™ A 1000 or A 5000 (available from Grindsted Products, Denmark) and AMYLASE H or AMYLASE P (available from Gist-Brocades, The Netherlands). A commercially available glucose oxidase useful in the present invention is GLUZYME™ (an *Aspergillus niger* glucose oxidase, available from Novo Nordisk A/S, Denmark).

Commercially available proteases useful in the present invention are NEUTRASE™ (a *Bacillus amyloliquefaciens* endoprotease, available from Novo Nordisk A/S, Denmark) and GLUTENASE™ (available from Novo Nordisk A/S, Denmark). Commercially available pentosanases useful in the present invention are PENTOPAN™ (a *Humicola insolens* pentosanase, available from Novo Nordisk A/S, Denmark) and PENTOPAN™ MONO (a *Thermomyces lanuginosus* pentosanase, available from Novo Nordisk A/S, Denmark). A commercially available lipase useful in the present invention is NOVOZYM® 677 BG (a *Thermomyces lanuginosus* lipase, available from Novo Nordisk A/S, Denmark).

In the methods of the present invention for preparing a dough and/or baked product, a glutathione:dehydroascorbate dehydrogenase (E.C. 1.8.5.1) may be further incorporated into a dough and/or the baked product obtained from the dough.

When one or more additional enzyme activities are to be added in accordance with the methods of the present invention, these activities may be added separately or together with the dehydrogenase(s), optionally as constituent(s) of the bread-improving and/or dough-improving composition. The other enzyme activities may be any of the enzymes described above and may be dosed in accordance with established baking practices.

In addition to the above-mentioned additional enzymes, a dehydrogenase may contain varying minor amounts of other enzymatic activities inherently produced by the producer organism in question.

In addition, or as an alternative, to additional enzyme components, a conventionally used baking agent(s) may also be incorporated into the dough. The baking agent may include proteins, such as milk powder (to provide crust colour), gluten (to improve the gas retention power of weak flours), and soy (to provide additional nutrients and improve water binding); eggs such (either whole eggs, egg yolks or egg whites); fat such as granulated fat or shortening (to soften the dough and improve the texture of the bread); emulsifier (to improve dough extensibility and, to some extent, the consistency of the resulting bread); oxidant, e.g., ascorbic acid, potassium bromate, potassium iodate, azodicarbon amide (ADA) or ammonium persulfate (to strengthen the gluten structure); amino acid, e.g., L-cysteine (to improve mixing properties); sugar; salt, e.g., sodium chloride, calcium acetate, sodium sulfate or calcium sulphate (to make the dough firmer); flour; and starch. Such components may also be added to the dough in accordance with the methods of the present invention.

Examples of suitable emulsifiers are mono- or diglycerides, diacetyl tartaric acid esters of mono- or diglycerides, sugar esters of fatty acids, polyglycerol esters of fatty acids, lactic acid esters of monoglycerides, acetic acid esters of monoglycerides, polyoxyethylene stearates, phospholipids, and lecithin.

The dough and/or baked product prepared by a method of the present invention may be based on wheat meal or flour, optionally in combination with other types of meal or flour such as corn meal, corn flour, rye meal, rye flour, oat meal, oat flour, soy meal, soy flour, sorghum meal, sorghum flour, potato meal, or potato flour.

The handling of the dough and/or baking may be performed in any suitable manner for the dough and/or baked product in question, typically including the steps of kneading the dough, subjecting the dough to one or more proofing treatments, and baking the product under suitable conditions, i.e., at a suitable temperature and for a sufficient period of time. For instance, the dough may be prepared by using a normal straight dough process, a sour dough process, an overnight dough method, a low-temperature and long-time fermentation method, a frozen dough method, the Chorleywood Bread process, or the Sponge and Dough process.

From the above disclosure it will be apparent that the dough of the invention is generally a leavened dough or a dough to be subjected to leavening. The dough may be leavened in various ways such as by adding sodium bicarbonate or the like, or by adding a leaven (fermenting dough), but it is preferable that the dough be leavened by adding a suitable yeast culture, such as a culture of *Saccharomyces cerevisiae* (baker's yeast). Any of the commercially available *Saccharomyces cerevisiae* strains may be employed.

The present invention also relates to the use of a dehydrogenase(s) for the preparation of pasta dough, preferably prepared from durum flour or a flour of comparable quality. The dough may be prepared by use of conventional techniques and the dehydrogenase(s) used in a similar dosage as that described above. The dehydrogenase(s) may be any of the types described above. When used in the preparation of pasta, the dehydrogenase(s) results in a strengthening of the gluten structure, a reduction in the dough stickiness, and increased dough strength.

The present invention also relates to methods for preparing a baked product, comprising baking a dough obtained by a method of the present invention to produce a baked product. The baking of the dough to produce a baked product may be performed using methods well known in the art.

The present invention also relates to compositions comprising an effective amount of one or more dehydrogenases, and a carrier and/or a baking ingredient. The compositions may further comprise a substrate for the dehydrogenase(s), one or more additional enzymes, one or more conventionally used baking agents, an enzyme which acts on a substance endogenous to the flour to produce a substrate for the dehydrogenase(s) of interest, and/or a substance and the enzyme which acts on the substance to produce a substrate for the dehydrogenase(s).

The present invention also relates to doughs and baked products, respectively, produced by the methods of the present invention.

The present invention further relates to a pre-mix, e.g., in the form of a flour composition, for dough and/or baked products made from dough, in which the pre-mix comprises one or more dehydrogenases, wherein each dehydrogenase is independently:

(a) a NAD(P)-independent dehydrogenase selected from the group consisting of a donor:quinone dehydrogenase (E.C. 1.1.5 and 1.1.99), donor:cytochrome dehydrogenase (E.C. 1.1.2), aldehyde:pyrroloquinoline-quinone (E.C. 1.2.99.3); succinate:ubiquinone dehydrogenase (E.C. 1.3.5.1); succinate dehydrogenase (E.C. 1.3.99.1); primary amine dehydrogenase (E.C. 1.4.99.3); sarcosine dehydrogenase (1.5.99.1); dimethylglycine dehydrogenase (E.C. 1.5.99.2); nicotine dehydrogenase (E.C. 1.5.99.4); spermidine dehydrogenase (E.C. 1.5.99.6); proline dehydrogenase (E.C. 1.5.99.8); monodehydroascorbate reductase (E.C. 1.6.5.4); NAD(P)H:quinone dehydrogenase (E.C. 1.6.99.2); and ubiquinol:ferricytochrome-c dehydrogenase (E.C. 1.10.2.2); and (b) a NAD(P)-dependent dehydrogenase.

The term "pre-mix" is defined herein to be understood in its conventional meaning, i.e., as a mix of baking agents, generally including flour, which may be used not only in industrial bread-baking plants/facilities, but also in retail bakeries. The pre-mix may be prepared by mixing one or more dehydrogenases or a bread-improving and/or dough-improving composition of the invention comprising one or more dehydrogenases with a suitable carrier such as flour, starch, a sugar, or a salt. The pre-mix may contain other dough-improving and/or bread-improving additives, e.g., any of the additives, including enzymes, mentioned above. The pre-mix may further comprise a glutathione:dehydroascorbate dehydrogenase (E.C. 1.8.5.1).

The present invention even further relates to baking additives in the form of a granulate or agglomerated powder, which comprise one or more dehydrogenases, wherein each dehydrogenase is independently:

(a) a NAD(P)-independent dehydrogenase selected from the group consisting of a donor:quinone dehydrogenase (E.C. 1.1.5 and 1.1.99), donor:cytochrome dehydrogenase (E.C. 1.1.2), aldehyde:pyrroloquinoline-quinone (E.C. 1.2.99.3); succinate:ubiquinone dehydrogenase (E.C. 1.3.5.1); succinate dehydrogenase (E.C. 1.3.99.1); primary amine dehydrogenase (E.C. 1.4.99.3); sarcosine dehydrogenase (1.5.99.1); dimethylglycine dehydrogenase (E.C. 1.5.99.2); nicotine dehydrogenase (E.C. 1.5.99.4); spermidine dehydrogenase (E.C. 1.5.99.6); proline dehydrogenase (E.C. 1.5.99.8); monodehydroascorbate reductase (E.C. 1.6.5.4); NAD(P)H:quinone dehydrogenase (E.C. 1.6.99.2); and ubiquinol:ferricytochrome-c dehydrogenase (E.C. 1.10.2.2); and (b) a NAD(P)-dependent dehydrogenase.

The baking additives may further comprise a glutathione: dehydroascorbate dehydrogenase (E.C. 1.8.5.1). The baking additive preferably has a narrow particle size distribution with more than 95% (by weight) of the particles in the range from 25 to 500 μm.

The present invention is further described by the following examples that should not be construed as limiting the scope of the invention.

EXAMPLES

Materials and Methods

Preparation of White Bread (I)

The straight-dough bread-making method may be used according to AACC Method 10-10B (in Approved Methods of the American Association of Cereal Chemists, Ninth Edition, March 1995; AACC, St. Paul, Minn., USA).

| Basic recipe | |
| --- | --- |
| Wheat flour | 100% |
| Salt | 1.5% |
| Yeast (fresh) | 5.3% |
| Sugar | 6.0% |

| -continued | |
| --- | --- |
| Basic recipe | |
| Shortening | 3.0% |
| Water | optimum |

All percentages are by weight relative to the wheat flour.

Procedure

1. Dough mixing (Hobart mixer):
   The mixing time and speed should be determined by the skilled baker so as to obtain an optimum dough consistency under the testing conditions used.
2. 1st punch (e.g., 52 minutes after start)
3. 2nd punch (e.g., 25 minutes later)
4. Molding and panning (e.g., 13 minutes later).
5. Proofing to desired height (e.g., 33 minutes at 32° C., 82% RH)
6. Baking (e.g., at 215° C. for 24 minutes)

Preparation of White Bread (II)

The sponge-dough bread-making method may be used according to AACC Method 10-11 (in Approved Methods of the American Association of Cereal Chemists, Ninth Edition, March 1995; AACC, St. Paul, Minn., USA).

| Basic recipe for Sponge | |
| --- | --- |
| Wheat flour | 60% |
| Yeast (compressed) | 36% |
| Yeast Food | 2% |
| Water | 36% |

All percentages are by weight relative to the wheat flour.

Procedure

1. Add water to compressed yeast
2. Add yeast food in dry form with flour
3. Mix sponge (Hobart A-120; Hobart Corp., Troy, Ohio, USA):
   0.5 minute at $1^{st}$ speed
   1 minute at $2^{nd}$ speed
   The mixing time may be adjusted so as to obtain an optimum dough consistency under the testing conditions used.
4. Ferment in a fermentation cabinet: 4 hours at 30° C., 85% RH

| Basic recipe for Dough | |
| --- | --- |
| Wheat flour | 40% |
| Water | 24% |
| Sugar | 5% |
| Shortening | 3% |
| Salt | 2% |

All percentages are by weight relative to the wheat flour.

Procedure

1. Add dough ingredients; begin mixer ($1^{st}$ speed)
2. Add sponge in three approximately equal portions at 15, 25, and 35 seconds mixing time; total mixing time: 1 minute
3. At $2^{nd}$ speed, mix to obtain an optimum dough consistency
4. Ferment in a fermentation cabinet: 30 minutes at 30° C., 85% RH
5. Intermediate proof: 12–15 minutes in fermentation cabinet 6. Mold and final proof at 35.5° C., 92% RH
7. Bake: 25 minutes at 218° C.

Evaluation of Staling Properties of Bread

The degree of staling is determined on bread, e.g., on day 1, 3, 7 and 9 after baking. Evaluation of staleness and texture can be done according to AACC method 74-09. The principles for determination of softness and elasticity of bread crumb are as follows:

1. A slice of bread is compressed with a constant speed in a texture analyser, measuring the force for compression in g.
2. The softness of the crumb is measured as the force at 25% compression.
3. The force at 40% compression (P2) and after keeping 40% compression constant for 30 seconds (P3) is measured. The ratio (P3/P2) is the elasticity of the crumb.

Preparation of White Layer Cake

The method may be used according to AACC Method 10-90 (in Approved Methods of the American Association of Cereal Chemists, Ninth Edition, March 1995; AACC., St. Paul, Minn., USA).

| Basic recipe | |
|---|---|
| Flour | 100% |
| Sugar | 140% |
| Shortening | 50% |
| Nonfat Dry Milk | 12% |
| Dried Egg Whites | 9% |
| Salt | 3% |
| Baking Powder and Water | determined empirically |

All percentages are by weight relative to the flour.

Procedure
1. Combine all dry ingredients and sift well
2. Add shortening and 60% of water
3. Mix at low speed for 0.5 minute in Hobart C-100 mixer
4. Mix at medium speed for 4 minutes
5. Add 50% of remaining water
6. Mix at low speed for 0.5 minute, scrape down and mix at medium speed for 2 minutes
7. Add remaining water, mix at low speed for 0.5 minute, scrape down and mix at medium speed for 2 minutes
8. Scale batter into each of two greased pans
9. Bake at 375° C. or 350° C.

Evaluation of Cakes

Cakes should be graded for volume and texture on the same day as baked according to AACC Method 10-90.

The internal structure may be scored for the uniformity and size of cells as well as thickness of the walls; the grain; texture, such as moisture, tenderness and softness; crumb colour; and flavour.

Preparation of Cookies

Cookies may be prepared according to AACC Method 10-50D (in Approved Methods of the American Association of Cereal Chemists, Ninth Edition, March 1995; AACC., St. Paul, Minn., USA).

| Basic recipe | |
|---|---|
| Flour | 225 g |
| Water | 16 g |
| Dextrose Solution | 33 g |
| Bicarbonate of Soda | 2.5 g |
| Salt | 2.1 g |
| Sugar | 130 g |
| Shortening | 64 g |

Procedure
1. Cream shortening, sugar, salt and soda on low speed 3 minutes using an electric mixer (e.g., Hobart C-100)
2. Add dextrose solution and distilled water
3. Mix at low speed for 1 minute
4. Mix at medium speed for 1 minute
5. Add all flour and mix at low speed for 2 minutes
6. Scrape dough from bowl and place six portions at well-spaced points on lightly greased cookie sheet
7. Flatten dough lightly
8. Cut dough with cookie cutter
9. Bake at 205° C. for 10 minutes Evaluation of Cookies Cookie width should be measured after cooling 30 minutes and can be done by the method according to AACC Method 10-50D.

The width of each of the six cookies is measured in mm, then rotated 90° and remeasured to obtain the average width (W). An average thickness (T) may be obtained by measuring the cookies stacked on top of one another, then restacked in a different order. The spread factor is the ratio of W/T. However, the most sensitive and reliable estimate is the width measurement, and in some cases, thickness. Because the spread factor is a ratio of 2 empirically determined parameters, different values of W and T can result in the same W/T.

Preparation of Biscuits

Biscuits may be prepared according to AACC Method 10-31B (in Approved Methods of the American Association of Cereal Chemists, Ninth Edition, March 1995; AACC., St. Paul, Minn., USA).

| Basic recipe | |
|---|---|
| Flour | 228 g |
| Shortening | 40 g |
| Milk Solution[1] | 135 g |
| Bicarbonate of Soda[2] | 3.4 g |
| Salt[2] | 4.5 g |
| Monocalcium Phosphate[2] | 130 g |

[1] 50 g milk powder in 450 ml water
[2] omit if self-rising flour is used; use 240 g of self-rising flour Procedure
1. Sift together flour and other dry ingredients (bicarbonate of soda, salt and monocalcium phosphate, if used)
2. Add shortening to flour mixture
3. Mix, using electric mixer (e.g., Hobart, Kitchen Aid or equivalent) with timer control, at speed 1 for 15 seconds
4. Mix at speed 1 for 3 minutes
5. Add milk solution and mix at speed 1 for 15 seconds
6. Roll out dough using floured rolling pin
7. Cut dough with floured cutter
8. Place 8 dough pieces 4 cm apart on ungreased baking sheet.
9. Bake at 232° C. for 10 minutes Evaluation of Biscuits Upon removal from oven, biscuits should be removed from the baking sheet and cooled for 30 minutes. Measurements of the eight biscuits can be made according to AACC Method 10-31B to obtain a total weight, a total diameter and a height at the top center of each biscuit.

Preparation of Pie Shells

Pie shells may be prepared according to AACC Method 10-60 (in Approved Methods of the American Association of Cereal Chemists, Ninth Edition, March 1995; AACC., St. Paul, Minn., USA).

| Basic recipe | |
|---|---|
| Flour | 100 % |
| Shortening | 60 % |
| Salt | 3.5 % |
| Water | 30–64 % |

All percentages are by weight relative to the wheat flour, and all ingredients are at 10° C. before mixing.

Procedure
1. Sift flour twice
2. Add shortening to flour and cut for 5 minutes using electric mixer (e.g., Hobart, Kitchen Aid or equivalent) with timer control, on low speed
3. Dissolve salt in a portion of water
4. Add salt solution to flour-shortening mixture, together with additional water if necessary
5. Mix at low speed for 2 minutes
6. Store dough at 10° C. for 24 hours
   Empty Shells
7. Scale, press dough into ball
8. Roll dough, fold and roll again
9. Fold and roll a third time
10. Lay dough sheet over an inverted pie tin
11. Trim dough and prick with fork
12. Let dry for 30 minutes and cover with a second pan pressed down firmly
13. Bake at 218° C. for 20–25 minutes, removing second pan after 10 minutes in the oven
    Filled Pies
7. Scale and roll bottom crust as outlined above for empty pie shell
8. Press dough sheet into pie tin and fill with either artificial fruit acid filling (water, corn starch, sugar and citric acid crystals) or true fruit filling (cling peaches, sugar corn starch and water)
9. Scale and roll dough once for top crust
10. Place over filling, trim and cut center lightly
11. Press edge over wetted edge of bottom crust
12. Bake at 218° C. for about 30 minutes Evaluation of Pie Crusts Viscosity may be evaluated according to AACC Method 56-80. Other parameters of empty and filled pie shells may be measured according to AACC Method 10-60 24 hours and 12 or 16 hours after baking, respectively. Pie crusts may be evaluated empirically for whether they are baked through; the edges have shrunk from edge of pan; blisters have appeared; the texture is flaky; the mouth-feel is tender; whether they are crisp or soft; the colour; and if the fruit filling has penetrated the crust.

Testing of Doughs and Breads

According to the methods of the present invention, the effect of adding a dehydrogenase may be tested in doughs and breads by using the following method:

| Recipe: | |
|---|---|
| Water | 60% |
| Wheat Flour | 100% |
| Yeast | 4% |
| Salt | 1.5% |
| Sugar | 1.5% |

The wheat flour is of the type Meneba 964.

Preparation of Breads

Procedure
1. Dough mixing (Spiral mixer)
   3 minutes at low speed
   8 minutes at high speed
   The mixing time may be adjusted by the skilled baker to obtain an optimum dough consistency under the testing conditions used.
2. 1st proof: 30° C.-80% RH, 20 minutes
3. Scaling and shaping;
4. Final proof: 32° C.-80% RH, 40 minutes;
5. Baking: 225° C., 20 minutes for rolls and 30 minutes for loaf.

Evaluation of Dough and Baked Products

Dough and baked products made from the straight dough method described above may be evaluated as follows for loaf specific volume, dough stickiness, dough firmness, dough extensibility, dough elasticity, crumb structure, and gluten strength.

Loaf specific volume: The mean value of 4 loaves volume are measured using the traditional rape seed method. The specific volume is calculated as volume ml per g bread. The specific volume of the control (without enzyme) is defined as 100. The relative specific volume index is calculated as:

$$\text{Specific vol. index} = \frac{\text{specific vol. of 4 loaves}}{\text{specific vol. of 4 control loaves}} \times 100$$

The dough stickiness, firmness, extensibility, elasticity and crumb structure may be evaluated relative to controls by the skilled test baker according to the following scale:

| | | |
|---|---|---|
| Dough stickiness: | almost liquid | 1 |
| | too sticky | 2 |
| | sticky | 3 |
| | normal | 4 |
| | dry | 5 |
| | too dry | 6 |
| Crumb structure: | very poor | 1 |
| | poor | 2 |
| | non-uniform | 3 |
| | uniform/good | 4 |
| | very good | 5 |
| Dough Firmness: | extremely soft | 1 |
| | too soft | 2 |
| | soft/good | 3 |
| | normal | 4 |
| | firm | 5 |
| | too firm | 6 |
| Dough Extensibility: | too short | 1 |
| | short | 2 |
| | normal | 3 |
| | good | 4 |
| | long | 5 |
| | too long | 6 |

Dough stability/Shock test: After the second proof a pan containing the dough is dropped from a height of 20 cm. The dough is baked and the volume of the resulting bread is determined.

Gluten Strengthening: The strengthening effect of a given dough conditioner on wheat flour dough or gluten dough may be measured by dynamic rheological measurements. These measurements are able to show the strength of a dough under oscillation. Both wheat flour dough and gluten dough are viscoelastic materials. In oscillatory measurements, the viscoelastic properties of a wheat dough and a gluten dough can be divided into two components, the dynamic shear storage modulus G' and the dynamic shear loss modulus G". The ratio of the loss and the storage moduli is numerically equal to the tangent of the viscoelastic phase angle δ (Delta). An increase in the storage modulus G' and a decrease in the phase angle δ indicate a stronger and more elastic dough.

Example 1
Purification of a Cellobiose Dehydrogenase

A solution of 9.52 kg of CELLUZYME™ (a *Humicola insolens* cellulolytic preparation, available from Novo Nordisk A/S, Bagsvard, Denmark) in 31.7 liters of water was stirred for 8 hours and then centrifuged to yield 23.15 liters of supernatant.

The cellobiose dehydrogenase was precipitated from the supernatant at 35% $(NH_4)_2SO_4$ and resuspended in water. By ultrafiltration with a H1P30–43 filter (Amicon, Beverly, Mass.), the solution was adjusted to a conductivity of 8.1 mS and a pH of 7.0.

A Q-Sepharose Big Beads (Pharmacia, Uppsala, Sweden) column (600 ml) was pre-equilibrated in 10 mM Tris pH 7.0 buffer. The ultrafiltered solution was loaded onto the column which was then washed with two column volumes of 10 mM Tris pH 7.0. The column was eluted using a gradient of 0.0 to 0.8 M NaCl in 10 mM Tris pH 7.0 buffer. The fractions were collected and assayed for cellobiose dehydrogenase activity using the microtiter assay described below and the active fractions were pooled.

The activity of cellobiose dehydrogenase was assayed with cellobiose and dichloroindophenol (DCPIP). On a microplate reader, 90 µl of color reagent containing 100 µM DCPIP (Sigma Chemical Co., St. Louis, Mo.), 250 µM cellobiose (Sigma Chemical Co., St. Louis, Mo.), and 93 mM sodium phosphate pH 7.5 buffer was mixed with 10 µl of enzyme sample (diluted in water). The absorbance at 600 nm was measured using the plate reader at 10, 15, 20, 25 and 30 minutes after the mixing of the color reagent and the enzyme sample. The assay was performed at room temperature. A linear regression analysis yielded the change in absorbance as mOD/min.

Using a spectrophotometer, DCPIP color reagent (900 µl) was added to 100 µl of enzyme sample (diluted in water) and the absorbance at 600 nm was measured at 10, 15, 20, 25 and 30 minutes after the mixing of the color reagent and the enzyme sample. The assay was performed at 40° C. Linear regression analysis provided the change in absorbance as $cm^{-1}$/minute, which was proportional to the concentration of enzyme in the sample.

All the active fractions were concentrated and washed using an Amicon PM30 membrane (Amicon, Beverly, Mass.) to a conductivity of 1.1 mS. The pH was adjusted to 5.0.

A SP-Sepharose Fast Flow column (Pharmacia, Uppsala, Sweden) (180 ml) was pre-equilibrated with 10 mM sodium citrate pH 5.0 buffer. The pool described above was loaded onto the column and the flow-through collected. The flow-through contained cellobiose dehydrogenase activity.

The pH of the flow-through was adjusted to 7.0 and $(NH_4)_2SO_4$ was added to a concentration of 0.7 M. A Phenyl Sepharose (Pharmacia, Uppsala, Sweden) column was pre-equilibrated with 1.7 M $(NH_4)_2SO_4$-50 mM sodium phosphate pH 7.0. The SP-Sepharose flow-through was loaded onto the column and the column was washed using 0.85 M $(NH_4)_2SO_4$-50 mM sodium phosphate pH 7.0. The protein was eluted using a gradient from 0.85 to 0.0 M $(NH_4)_2SO_4$ in 50 mM sodium phosphate pH 7.0 followed by 50 mM sodium phosphate pH 7.0 and then pure water. Fractions were collected and assayed as described above. Two groups of active fractions were identified: One from the 50 mM sodium phosphate pH 7.0 and the other from the water elution. These fractions was pooled into two different pools. Both were concentrated and washed with water using ultrafiltration (PM30 membrane). The concentrates were diluted with 10 mM Tris pH 7.0 and designated Phe1 and Phe2.

A 20 ml HR 16/10 Mono Q column (Pharmacia, Uppsala, Sweden) was pre-equilibrated with 10 mM Tris pH 7.0. Phe1 was loaded onto the column and the loaded column was washed with 10 mM Tris pH 7.0. The column was then eluted with a gradient of 0.0 to 0.5 M NaCl in 10 mM Tris pH 7.0. The fractions were assayed for activity as described above and pooled. The same procedure was conducted with Phe2 except that a 0.15 to 0.40 M NaCl gradient was used.

On SDS-PAGE, the cellobiose dehydrogenase from Phe1 had a slightly higher mobility than the cellobiose dehydrogenase from Phe2. However, both forms had a molecular weight of around 90 kDa.

The extinction coefficients for a 1 mg/ml solution of cellobiose dehydrogenase are $A_{280}=3.88$ $cm^{-1}$ and $A_{420}=2.39$ $cm^{-1}$. The $K_m$ and $k_{cat}$ at pH 7.5, 40° C. were determined to be $K_m=11$ µM, $k_{cat}=10$ $s^{-1}$ for cellobiose and $K_m=26$ µM, $k_{cat}=12$ $s^{-1}$ for DCPIP.

Example 2
Baking Test with Purified Cellobiose Dehydrogenase

About 2 ml of the purified cellobiose dehydrogenase (4.8 mg or $3.8 \times 10^4$ U in 10 mM Tris, pH 7) described in Example 1 was mixed with flour and other ingredients in a Welbilt bread machine Model ABM6000 (Welbilt, Great Neck, N.Y.) according to the bread-making protocol described below. One cellobiose dehydrogenase unit (CBDU) is the amount of enzyme which converts 1.0 micromole of cellobiose or DCPIP per minute at pH 7.5 and 25° C. A control was run in which 2 ml of 10 mM Tris pH 7 buffer was used in place of the enzyme.

Basic White Bread

Dough: Robin Hood flour, 508 g; $H_2O$, 276 g; Fleischmann yeast, 9 g; sugar, 34 g; salt, 11 g; Crisco vegetable oil, 32 ml; Carnation nonfat dry milk, 14 g.

Protocol: Mix (first kneading) for 15 minutes

Rise (first) for 32 minutes

Mix (second kneading) for 23 minutes

Rise (second) for 20 minutes

Punch down for 2 seconds

Rise (third) for 65 minutes

Bake for 55 minutes (all steps automated in the Welbilt bread machine)

Loaf volume was determined as described in the methods section.

The results showed that cellobiose dehydrogenase increased the loaf volume 4% relative to the control.

Example 3
Properties of Dough and Bread with Purified Cellobiose Dehydrogenase

The purified cellobiose dehydrogenase was evaluated in a micro-baking assay to determine its effect on stickiness and firmness of the dough and loaf volume and crumb structure of the bread.

The dough was prepared by mixing water, 60%; wheat flour, 100% (Type Meneba 964); yeast, 4%; salt, 1.5%; and sugar, 1.5% in a 10 g Micro Mixer (type NSI-33R, from National Manufacturing Co.) for 2.5 minutes. Enzyme was added before mixing at a dosage of 5–50 mg per kg flour. Lactose and cellobiose were each added at 5 g/kg flour. The final dough temperature after mixing was approximately 27° C. The dough was evaluated for stickiness and firmness immediately after mixing according to the method described in the methods section.

The micro-baking assay was conducted as follows:

| Point | Micro-Baking European straight dough and panned bread | |
|---|---|---|
| | Stage | Time, minutes |
| A | After mixing in gear I | 3.0 |
| B | After mixing in gear II | 6.5 |
| C | After first fermentation | 25.8 |
| D | Before panning | 46.5 |
| E | 50% proofing | — |
| F | Before baking | 103.5 |
| G | After 10 minutes baking | 113.5 |
| H | After 20 minutes baking | 123.5 |
| J | After baking | 138.5 |

The results shown below in Table 1 demonstrated that with lactose and cellobiose added as substrates for cellobiose dehydrogenase, significant effects were produced with the enzyme in a dosage range from 5–50 mg per kg flour. At a dosage of 50 mg protein/kg flour, the cellobiose dehydrogenase produced positive effects on volume, stickiness, and firmness.

TABLE 1

| Parameter | No Enzyme | CBD 5 mg/kg | CBD 15 mg/kg | CBD 50 mg/kg |
|---|---|---|---|---|
| Volume | 4.0a | 3.9a | 3.9a | 4.1b |
| Stickiness | 2.5a | 3.8b | 4.1c | 4.5d |
| Firmness | 2.5a | 3.8b | 4.1c | 4.5d |

Treatments marked with identical letters can not be statistically distinguished (on a 5% level of significance).

Example 4

Properties of Dough and Bread to which Fructose Dehydrogenase was Added

A Gluconobacter sp. D-fructose dehydrogenase (Sigma Chemical Co., St. Louis, Mo., product F-5152; EC 1.1.99.11, with 20 U/mg solid) was evaluated using the micro-baking assay described in Example 3. D-fructose dehydrogenase was added at dosages of 50, 500, and 5000 U per kg flour. One unit (U) of D-fructose dehydrogenase will convert 1 micromole of D-fructose to 5-keto-D-fructose per minute at pH 4.5 at 37° C. D-fructose was also added at 1.8 g/kg flour.

The results shown below in Table 2 demonstrated that the fructose dehydrogenase induced a positive effect on crumb structure when dosed at 50 and 500 U/kg, and a positive effect on anti-stickiness when dosed at 500 and 5000 U/kg.

TABLE 2

Effect of fructose dehydrogenase

| | | Fructose dehydrogenase | | |
|---|---|---|---|---|
| | No Enzyme Added | 50 U/kg | 500 U/kg | 5000 U/kg |
| Stickiness | 3.75a | 3.50a | 4.12b | 6.00c |
| Crumb structure | 3.00a | 3.62b | 3.40b | 3.00a |

Treatments marked with identical letters can not be statistically distinguished (on a 5% level of significance).

Example 5

Properties of Dough and Bread to which Lactic Dehydrogenase was Added

A Saccharomyces cerevisiae L-lactic dehydrogenase (cytochrome b2) (Sigma Chemical Co., St. Louis, Mo., product L4506; EC 1.1.2.3, with 0.1–0.6 U/mg protein) was evaluated in the micro-baking assay described in Example 3. L-lactic dehydrogenase (cytochrome b2) was dosed at 10, 100, and 1000 U per kg flour. One unit (U) of L-lactic dehydrogenase will oxidize 0.5 micromole of L-lactic acid to pyruvate per minute at pH 8.4 at 37° C. L-lactic acid was also added at 1.8 g/kg flour.

The results shown in Table 3 demonstrated that L-lactic dehydrogenase (cytochrome b2) induced positive effects on the loaf volume, crumb structure, and stickiness (firmness) when dosed at 1000 U/kg.

TABLE 3

Effect of lactic dehydrogenase (cytochrome b2)

| | | lactic dehydrogenase | | |
|---|---|---|---|---|
| | No Enzyme Added | 10 U/kg | 100 U/kg | 1000 U/kg |
| Volume | 3.65a | 3.68a | 3.69a | 3.83b |
| Stickiness | 3.16a | 3.50a | 3.18a | 4.00b |
| Crumb structure | 2.8a | 3.0b | 2.7a | 3.3c |

Treatments marked with identical letters can not be statistically distinguished (on a 5% level of significance).

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended any of claims.

Various references are cited herein, the disclosures of which are incorporated by reference in their entireties.

What is claimed is:

1. A method for preparing a dough, comprising incorporating into the dough an effective amount of one or more dehydrogenases, wherein the effective amount of each dehydrogenase is about 0.01 mg to about 100 mg per kilogram of dough and each dehydrogenase is independently:
    (a) a NAD(P)-independent dehydrogenase selected from the group consisting of a donor:quinone dehydrogenase (E.C. 1.1.5 and 1.1.99), donor:cytochrome dehydrogenase (E.C. 1.1.2), aldehyde:pyrroloquinoline-quinone (E.C. 1.2.99.3); succinate:ubiquinone dehydrogenase (E.C. 1.3.5.1); succinate dehydrogenase (E.C. 1.3.99.1); primary amine dehydrogenase (E.C. 1.4.99.3); sarcosine dehydrogenase (1.5.99.1); dimethylglycine dehydrogenase (E.C. 1.5.99.2); nicotine dehydrogenase (E.C. 1.5.99.4); spermidine dehydrogenase (E.C. 1.5.99.6); proline dehydrogenase (E.C. 1.5.99.8); monodehydroascorbate reductase (E.C. 1.6.5.4); NAD(P)H:quinone dehydrogenase (E.C. 1.6.99.2); and ubiquinol:ferricytochrome-c dehydrogenase (E.C. 1.10.2.2); or (b) a NAD(P)-dependent dehydrogenase.

2. The method of claim 1, wherein the one or more dehydrogenases improve one or more properties of the dough or a baked product obtained from the dough.

3. The method of claim 1, wherein the one or more dehydrogenases improve one or more properties of the dough and a baked product obtained from the dough.

4. The method of claim 1, wherein the donor:quinone dehydrogenase is selected from the group consisting of a cellobiose dehydrogenase (E.C. 1.1.5.1), choline dehydrogenase (E.C. 1.1.99.1), D-gluconate dehydrogenase (E.C. 1.1.99.3), 2-dehydro-D-gluconate dehydrogenase (E.C. 1.1.99.4), glycerol-3-phosphate dehydrogenase (E.C. 1.1.99.5), D-2-hydroxy acid dehydrogenase (E.C. 1.1.99.6), alcohol dehydrogenase (E.C. 1.1.99.8), pyrodoxine dehydrogenase (E.C. 1.1.99.9), glucose dehydrogenase (E.C. 1.1.99.10), fructose 5-dehydrogenase (E.C. 1.1.99.11), sorbose dehydrogenase (E.C. 1.1.99.12), glucoside-3 dehydrogenase (E.C. 1.1.99.13), glycolate dehydrogenase (E.C. 1.1.99.14), malate dehydrogenase (E.C. 1.1.99.16), glucose:(pyrroloquinoline-quinone) dehydrogenase (E.C. 1.1.99.17), cellobiose dehydrogenase (E.C. 1.1.99.18), alkan-1-ol dehydrogenase (E.C. 1.1.99.20), D-sorbitol dehydrogenase (E.C. 1.1.99.21), glycerol dehydrogenase (E.C. 1.1.99.22), maltose dehydrogenase, pyranose 2-dehydrogenase, and glucose 3-dehydrogenase.

5. The method of claim 1, wherein the donor:cytochrome dehydrogenase is a lactate dehydrogenase (cytochrome) (E.C. 1.1.2.3) or mannitol dehydrogenase (E.C. 1.1.2.2).

6. The method of claim 1, wherein the donor:quinone dehydrogenase is a cellobiose dehydrogenase.

7. The method of claim 1, wherein the donor:quinone dehydrogenase is a fructose dehydrogenase.

8. The method of claim 1, wherein the donor:cytochrome dehydrogenase is a lactate dehydrogenase.

9. The method of claim 1, wherein the effective amount of the dehydrogenase is about 0.5 mg to about 5 mg per kilogram of dough.

10. The method of claim 9, wherein the effective amount of the dehydrogenase is about 0.5 mg to about 5 mg per kilogram of dough.

11. The method of claim 10, wherein the effective amount of the dehydrogenase is about 1 mg to about 5 mg per kilogram of dough.

12. The method of claim 2, wherein the one or more improved properties are selected from the group consisting of increased strength of the dough, increased stability of the dough, reduced stickiness of the dough, improved machinability of the dough, increased volume of the baked product, improved crumb structure of the baked product, improved softness of the baked product, improved flavor of the baked product, and improved antistaling of the baked product.

13. The method of claim 1, further comprising incorporating one or more additional enzymes selected from the group consisting of an amylase, cellulase, cyclodextrin glucanotransferase, glycosyltransferase, hemicellulase, laccase, lipase, oxidase, pentosanase, peptidase, peroxidase, phospholipase, protease, protein disulfide isomerase, and transglutaminase.

14. The method of claim 1, further comprising incorporating a glutathione:dehydroascorbate dehydrogenase (EC 1.8.5.1).

15. The method of claim 1, further comprising incorporating one or more additives selected from the group consisting of a protein, emulsifier, granulated fat, oxidant, amino acid, sugar, salt, flour, and starch.

16. A method for preparing a baked product, comprising baking a dough produced by the method of claim 1 to produce a baked product, wherein the one or more dehydrogenases improve one or more properties of the baked product.

17. The method of claim 16, wherein the one or more improved properties are selected from the group consisting of increased strength of the dough, increased stability of the dough, reduced stickiness of the dough, improved machinability of the dough, increased volume of the baked product, improved crumb structure of the baked product, improved softness of the baked product, improved flavor of the baked product, and improved antistaling of the baked product.

18. A dough product obtained from a dough prepared by the method of claim 1.

19. A baked product produced by the method of claim 16.

20. A composition comprising an effective amount of a baking agent and one or more dehydrogenases for improving one or more properties of a dough or a baked product obtained from the dough, wherein the effective amount of each dehydrogenase is about 0.01 mg to about 100 mg per kilogram of dough and each dehydrogenase is independently:

(a) a NAD(P)-independent dehydrogenase selected from the group consisting of a donor:quinone dehydrogenase (E.C. 1.1.5 and 1.1.99), donor:cytochrome dehydrogenase (E.C. 1.1.2), aldehyde:pyrroloquinoline-quinone (E.C. 1.2.99.3); succinate:ubiquinone dehydrogenase (E.C. 1.3.5.1); succinate dehydrogenase (E.C. 1.3.99.1); primary amine dehydrogenase (E.C. 1.4.99.3); sarcosine dehydrogenase (1.5.99.1); dimethylglycine dehydrogenase (E.C. 1.5.99.2); nicotine dehydrogenase (E.C. 1.5.99.4); spermidine dehydrogenase (E.C. 1.5.99.6); proline dehydrogenase (E.C. 1.5.99.8); monodehydroascorbate reductase (E.C. 1.6.5.4); NAD(P)H:quinone dehydrogenase (E.C. 1.6.99.2); and ubiquinol:ferricytochrome-c dehydrogenase (E.C. 1.10.2.2); or (b) a NAD(P)-dependent dehydrogenase.

21. The composition of claim 20, wherein the one or more dehydrogenases improve one or more properties of the dough and the baked product obtained from the dough.

22. The composition of claim 20, wherein the one or more improved properties are selected from the group consisting of increased strength of the dough, increased stability of the dough, reduced stickiness of the dough, improved machinability of the dough, increased volume of the baked product, improved crumb structure of the baked product, improved softness of the baked product, improved flavor of the baked product, and improved antistaling of the baked product.

23. The composition of claim 20, wherein the composition further comprises one or more additional enzymes selected from the group consisting of an amylase, cellulase, cyclodextrin glucanotransferase, glycosyltransferase, hemicellulase, laccase, lipase, oxidase, pentosanase, peptidase, peroxidase, phospholipase, protease, protein disulfide isomerase, and transglutaminase.

24. The composition of claim 20, wherein the composition further comprises a glutathione:dehydroascorbate dehydrogenase (E.C. 1.8.5.1).

* * * * *